United States Patent [19]

Gray et al.

[11] Patent Number: 4,632,515

[45] Date of Patent: Dec. 30, 1986

[54] HETEROCYCLICALLY SUBSTITUTED ETHANES AND THEIR USE IN LIQUID CRYSTAL MATERIALS AND DEVICES

[75] Inventors: George W. Gray, Cottingham; Beatrice M. Nicholas, South Harrow, both of England

[73] Assignee: The Secretary of State for Defence in Her Britannic Majesty's Government of the United Kingdom of Great Britain and Nothern Ireland, London, England

[21] Appl. No.: 688,987

[22] Filed: Jan. 4, 1985

[30] Foreign Application Priority Data

Jan. 11, 1984 [GB] United Kingdom ................. 8400665

[51] Int. Cl.$^4$ ......................... C09K 19/34; G02F 1/13; C07D 239/26; C07D 319/06
[52] U.S. Cl. ............................. 350/350 R; 252/299.5; 252/299.61; 350/350 S; 544/242; 544/298; 544/335; 549/369
[58] Field of Search ...................... 252/399.61, 299.63, 252/299.5; 350/350 R, 350 S; 544/298, 335, 242; 549/369

[56] References Cited

U.S. PATENT DOCUMENTS

| 4,439,015 | 3/1984 | Rich et al. ...................... 252/299.63 |
| 4,482,472 | 11/1984 | Carr et al. ...................... 252/299.5 |
| 4,512,636 | 4/1985 | Andrews et al. .............. 252/299.61 |
| 4,556,745 | 12/1985 | Carr et al. ...................... 252/299.63 |

FOREIGN PATENT DOCUMENTS

| 58981 | 9/1982 | European Pat. Off. .......... 252/299.5 |
| 84194 | 7/1983 | European Pat. Off. ........ 252/299.61 |
| 87679 | 9/1983 | European Pat. Off. ........ 252/299.61 |
| 149208 | 7/1985 | European Pat. Off. ........ 252/299.63 |
| 3225290 | 1/1984 | Fed. Rep. of Germany ........................ 252/299.61 |
| 3404116 | 8/1985 | Fed. Rep. of Germany ........................ 252/299.63 |
| 2092169 | 8/1982 | United Kingdom ............ 252/299.61 |

OTHER PUBLICATIONS

Gray, G. W., Mol. Cryst. Liq. Cryst., vol. 63, pp. 3–18, (1981).
Gray, G. W., et al., Mol. Cryst. Liq. Cryst., vol. 53, pp. 147–166, (1979).

*Primary Examiner*—Teddy S. Gron
*Attorney, Agent, or Firm*—Cushman, Darby & Cushman

[57] ABSTRACT

A heterocyclically substituted ethane having a formula:

$$R_1—Cy—CH_2.CH_2—A—R_2 \qquad \text{Formula I}$$

wherein
A represents a heterocyclic ring selected from a trans 2,5 disubstituted 1,3 dioxan ring and a 2,5 disubstituted 1,3-pyrimidine ring;
$R_1$ represents an alkyl group having from 1 to 15 carbon atoms and $R_2$ represents a group selected from hydrogen, alkyl having from 1 to 15 carbon atoms and alkoxy having from 1 to 15 carbon atoms provided that where A is a trans 2,5 disubstituted 1,3 dioxan ring $R_2$ is alkyl; and
Cy represents a trans-1,4 disubstituted cyclohexane ring.

4 Claims, 15 Drawing Figures

FORMULA Ia

FORMULA Ib

FORMULA Ic

FORMULA Id

FORMULA IIa

FORMULA IIb

FORMULA IIc

FORMULA IId

FORMULA IIe

FORMULA IIf

FORMULA IIg

FORMULA IIh

FORMULA IIi

FORMULA IVa

FORMULA IVb

FORMULA IVc

FORMULA IVd

FORMULA IVe

FORMULA IVf

FORMULA IVg

FORMULA IVh

FORMULA IVi

FORMULA IVj

FORMULA IVk

FORMULA IVl

FORMULA IVm

FORMULA IVn

HETEROCYCLICALLY SUBSTITUTED ETHANES AND THEIR USE IN LIQUID CRYSTAL MATERIALS AND DEVICES

The present invention relates to heterocyclically substituted ethanes and their use in liquid crystal materials and devices.

The use of liquid crystal materials to exhibit electro-optical effects in display devices such as digital calculators, watches, meters and simple word displays is now well known. However, known liquid crystal materials are not ideal in all respects and a considerable amount of work is currently being carried out in the art to improve their properties.

Liquid crystal materials normally consist of specially selected mixture compositions and improved materials are obtained by forming new mixtures having an improved combination of properties, eg by the provision of new compounds for incorporation in the mixtures.

According to the present invention there is provided a heterocyclically substituted ethane having a formula:

$R_1$—Cy—$CH_2.CH_2$—A—$R_2$    Formula I wherein
- A represents a heterocyclic ring selected from a trans 2,5 disubstituted 1,3 dioxan ring and a 2,5 disubstituted 1,3 pyrimidine ring;
- $R_1$ represents an alkyl group having from 1 15 carbon atoms and $R_2$ represents a group selected from hydrogen, alkyl having from 1 to 15 carbon atoms and alkoxy having from 1 to 15 carbon atoms provided that where A is a trans 2,5 disubstituted 1,3 dioxan ring $R_2$ is alkyl; and
- Cy represents a trans-1,4 disubstituted cyclohexane ring.

The groups $R_1$ and $R_2$ where alkyl or alkoxy are preferably n-alkyl or n-alkoxy groups having from 1 to 10 desirably 1 to 7 carbon atoms.

In the accompanying drawings:
FIG. 1 is a list of examples of compounds embodying the invention;
FIG. 2 is a schematic flow diagram of an example of a route which may be used to prepare dioxan compounds embodying the present invention;
FIGS. 3 and 4 are schematic flow diagrams of examples of routes which may be used to prepare pyrimidine compounds embodying the present invention;
FIGS. 5 to 8 are lists of the generalised formulae of compounds which may be mixed with compounds embodying the present invention;
FIGS. 9 to 15 are diagrams illustrating the construction and operation of an electro-optical device embodying the invention. These Figures are described further below.

The sub-classes of compounds which are within the scope of Formula I are represented by their generalised formulae as listed in FIG. 1, wherein each $R_1$ is alkyl and each R is independently alkyl. These generalised formulae are Formulae Ia to Id respectively.

Compounds of Formula Ia shown in FIG. 1 may be prepared by Route A illustrated in FIG. 2. In FIG. 2 $R_1$ and $R_2$ are alkyl groups and OTs represents a toluene-4-sulphonate group.

Compounds of Formulae Ib and Ic may be prepared by Route B illustrated in FIG. 3 $R_1$ represents an alkyl group and $R_2$ represents an alkyl group or hydrogen.

Compounds of Formula Ic may be prepared by Route C illustrated in FIG. 4. In FIG. 4 $R_1$ represents an alkyl group and $R_2$ represents an alkoxy group.

The starting materials 3-(trans-4'-alkylcyclohexyl)-propyl amidine hydrochlorides for use in Step C2 in Route C may be prepared as in Route B shown in FIG. 3.

The procedures involved in the individual steps shown in FIGS. 2, 3 and 4 may be carried out using known procedures, the overall routes being new.

The compounds of Formula I show advantageous properties compared with known compounds of comparable structure. In particular, the compounds of Formula Ia show a low viscosity and low birefringence and are particularly useful in certain display applications such as cholesteric-to-nematic phase change effect devices as described below and also in devices of the kind described in UK Patent Specification No. 2123163A.

The compounds of formula A1 as follows:

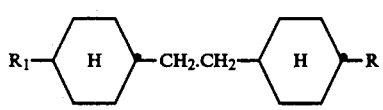

Formula A1 wherein $R_1$ and R are n-alkyl groups also show a low birefringence. However, the compounds of Formula I are generally more nematogenic and less smectogenic in nature than the compounds of Formula A1. This means that the compounds of Formula I are more attractive than the compounds of Formula A1 as low birefringence additives to nematic or chiral nematic mixtures for electro-optical displays. Also the compounds of Formula I advantageously have a more positive dielectric anisotropy than the Formula A1 compounds.

The compounds of Formula I have a relatively small dielectric anisotropy and may be added to liquid crystal materials of (greater) positive or negative dielectric anisotropy, known and referred to herein respectively as "positive" or "negative" materials in order to produce a mixture having amongst other things a suitable dielectric anisotropy. As is well known to those skilled in the art the dielectric anisotropy of the liquid crystal material is necessary to give electro-optical operation and its sign (for a given frequency) is chosen according to the kind of electro-optical device in which the material is to be used.

Compounds of reasonably low melting point are preferred as high dielectric anisotropy components. For example, the compounds of the classes whose generalised formulae are listed in FIG. 5 are suitable as positive materials.

In FIG. 5 each R is independently n-alkyl or n-alkoxy and each $R_4$ is independently n-alkyl.

Alternatively, or additionally, the compounds of Formula I may be added to other small dielectric anisotropy compounds, e.g. to reduce mixture melting points, viscosity or to improve multiplexibility. Examples of the generalised formulae of such other compounds are listed in FIG. 6.

In FIG. 6, each R is independently n-alkyl or n-alkoxy;
each $R_4$ is independently n-alkyl;
each R' is independently n-alkyl, n-alkoxy or hydrogen;
X=H or F; and
Q=halogen, e.g. Cl or F.

Thus, one or more compounds of Formula I may be added to one or more compounds of Formula IIa to IIi listed in FIG. 5 optionally together with one or more compounds of Formula IIIa to IIIn listed in FIG. 6.

Additional high clearing point compounds may be included in such mixtures, e.g. one or more compounds selected from the classes whose generalised formulae are listed in FIG. 7.

In FIG. 7 R, $R_A$, X and Y are as specified above.

Other specific known additives, e.g. chiral additives, such as

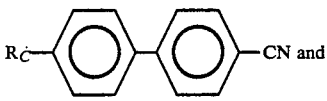

and

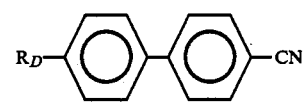

where $R_C=(+)$-2-methylbutyl and $R_D=(+)$-2-methylbutoxy, may be incorporated in the mixture where required.

The liquid crystal material obtained by blending together compounds of Formula I with those of the other classes as specified may be any one of the following:

(i) a positive nematic material for use in twisted nematic effect devices including multiplexed devices; an example of such a device is given below;

(ii) a negative material preferably also with a pleochroic dye, for use in Fréedericksz effect devices (negative nematic type) in which the molecular arrangement may be changed from the homeotropic texture (OFF state) to the homogeneous texture (ON state) by an electric field; an example of such a device is given below;

(iii) a positive nematic material, preferably also with a pleochroic dye, for use in Fréedericksz effect devices (positive nematic type) in which the molecular arrangement may be changed from the homogeneous texture (OFF state) to the homeotropic texture (ON state) by an electric field;

(iv) a negative material which is a cholesteric (chiral nematic) of suitable resistivity (about $10^9$ ohm-cm), for use in cholesteric memory mode devices in which the molecular arrangement may be changed from a homogeneous texture (OFF state) to a scattering focal conic texture (ON state) by an electric field;

(v) a strongly negative material which is a cholesteric, preferably together also with a pleochroic dye, for use in cholesteric-to-nematic phase change effect devices (positive contrast type) in which the molecular arrangement may be changed from a weakly scattering, i.e. clear, surface aligned homeotropic texture (OFF state) to a strongly scattering twisted homogeneous texture (ON state) by an electric field;

(vi) a positive material which is a cholesteric, preferably together also with a pleochroic dye, in cholesteric-to-nematic phase change effect devices (negative contrast type) in which the molecular arrangement may be changed from a scattering focal conic texture (OFF state) to a clear homeotropic texture (ON state) by an electric field;

(vii) a negative nematic material of suitable resistivity (about $10^9$ ohm-cm), in dynamic scattering effect devices in which the molecular arrangement may be changed from a clear homeotropic texture (OFF state) to a turbulent scattering texture (ON state) by an electric field;

(viii) a nematic material in two frequency switching effect devices (which may be twisted nematic effect devices) in which the dielectric anisotropy of the material may be changed from (at low frequency) positive (OFF state) to negative (ON state) by the application of a high frequency electric field;

(ix) a material suitable for the device described in copending UK Patent Specification No. 2123163A.

The construction and operation of the above devices and the general kinds of material which are suitable for use in them are themselves known.

Where a liquid crystal material is for use in a twisted nematic effect, cholesteric to nematic phase change effect (negative contrast type) or Fréedericksz effect (positive nematic type) device the material preferably contains:

Component A: one or more compounds of Formula I plus

Component B: one or more compounds of Formula IIa to IIi optionally together with one or more of the following:

Component C: one or more compounds of Formula IIIa to IIIn;

Component D: one or more compounds of Formula IVa to IVl;

Component E: one or more chiral additives.

For the twisted nematic effect and Fréedericksz (positive nematic) effect the following percentages of the various components may be used in the material (the overall sum of the percentages adding to 100%).

Component A: 5 to 95% by weight (typically 5 to 75% by weight)

Component B: 5 to 95% by weight (typically 10 to 50% by weight)

Component C: 0 to 90% by weight (typically 5 to 25% by weight)

Component D: 0 to 30% by weight (typically 0 to 20% by weight)

Component E: 0 to 5% by weight (typically 0 to 1% by weight)

For the phase change (negative contrast type) the following proportions may be used:

Components A to D: in the percentages as specified above;

Component E: 2 to 20% (typically 4 to 5%) by weight.

For the Fréedericksz (positive nematic) and phase change (negative contrast type) effects a pleochroic dye forming from 1.5 to 15% of the overall mixture is preferably added to the liquid crystal material. Suitable dyes are described in published UK Patent Application Nos. 2081736A, 208219A and 2093475A. Typically, each dye compound incorporated forms 1 to 3% by weight of the overall mixture.

Liquid crystal mixtures including compounds of Formula I may be formed in a known way, e.g. simply by heating the constituent compounds together in the correct weight proportion to form an overall isotropic liquid (e.g. about 100° C.).

To provide a more general example of a mixture embodying the invention at least one compound according to Formula I above may be mixed together with one or more compounds in any one or more of the known families listed in FIG. 8 for use in one or more of the applications given above (the actual application(s) depending on the mixture's properties):

In FIG. 8 each X is a 1,4 phenylene group, a 4,4'biphenylyl group, a 2,6 naphthyl group or a trans-1,4-disubstituted cyclohexane ring, and $Y_1$ is CN, or R' or halogen or CO.O—X—$Y^1$ where $Y^1$ is CN, or R' or OR'; where R and R' are alkyl groups; the compound may alternatively be a derivative of one of those listed in FIG. 8 wherein H is replaced by a halogen, e.g. F, in one or more of the benzene rings of the structure.

Preferably, the compound(s) of Formula I comprises between 5 and 95% by weight of the mixture.

According to the present invention in a second aspect a liquid crystal device includes two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein, characterised in that the liquid crystal material consists of or includes a compound according to Formula I above.

The device according to the second aspect may be a twisted nematic effect device, which may or may not be operated in a multiplexed fashion, a cholesteric-to-nematic phase change effect device a Fréedericksz effect device or a two-frequency switching effect device, all constructed in a known manner or any of the other devices mentioned above. The various ways in which compounds according to Formula I may be used in these devices are outlined above and will be further apparent to those skilled in the art.

Examples of the preparation and properties of compounds of Formula I will now be given. In these Examples the following abbreviations are used:

mp=melting point;
bp=boiling point.

EXAMPLE 1

Use of Route A shown in FIG. 2 to prepare the compound of Formula Ia (FIG. 1) having $R_1$=n—$C_5H_{11}$ and $R_2$=n—$C_3H_7$. Step A1a etc as follows are examples of Step A1 etc.

Step A1a

The production of trans-4-pentylcyclohexane-1-carboxylic acid chloride from trans-4-pentylcyclohexane-1carboxylic acid.

The step is carried out using the standard literature method for the production of a carboxylic acid chloride from the corresponding acid as described by A. I. Vogel in the reference Textbook of Practical Organic Chemistry, 4th edition, page 498, (1978).

Step A2a

The production of trans-4-pentylcyclohexyl methanol from trans-4-pentylcyclohexane-1-carboxylic acid chloride This Step is carried out using the standard literature method for the reduction of an acid chloride to an alcohol as described by A. I. Vogel in the reference Textbook of Practical Organic Chemistry, 4th edition, page 304 (1978). The product, trans-4-n-pentylcyclohexylmethanol, has a bp=162° C. at 25 mmHg.

Step A3a

The production of trans-4-pentylcyclohexylmethyl toluene-4'-sulphonate from the methanol produced in Step A2a This Step is carried out using the standard literature method for the preparation of a toluene-4-sulphonate from an alcohol which is described by A. I. Vogel in the reference Textbook of Practival Organic Chemistry, 4th edition, page 654 (1978). The product, trans-4-n-Pentylcyclohexylmethyl toluene-4'-sulphonate (obtained in a yield of 80%) has mp=53°–55° C.

Step A4a

The production of diethyl trans-4-pentylcyclohexylmethylmalonate from the coresponding toluene-4'-sulphonate produced in Step A3a Diethyl malonate (0.21 mole) is added dropwise to a solution of sodium ethoxide in ethanol, (previously prepared by running dry ethonol (100 cm³) onto sodium metal (0.204 g atom). When the addition is complete the temperature is adjusted to 50° C. and the trans-4-pentylcyclohexylmethyl toluene-4'-sulphonate (0.204 mole) in ethanol (300 cm³) is added dropwise over 1 hour. The reaction mixture is then heated under reflux until neutral to universal indicator. The while precipitate of sodium toluene-4-sulphonate is then filtered off and washed with dry ethanol. The filtrate and washings are then combined and the solvent is removed in vacuo. The residue is then poured into water (150 cm³) and the mixture is shaken with ether (3×50 cm³). The combined ethereal layuers are washed with water (100 cm³), dried using $MgSO_4$ and then the solvent is removed in vacuo. The residue is purified by distillation under reduced pressure.

Diethyl trans-4-n-pentylcyclohexylmethylmalonate (60%) has bp=124°–130° C. at 0.05 mm Hg.

Step A5a

The production of 3-(trans-4'-pentylcyclohexyl propanoic acid from the corresponding diethyl trans-4-methylcyclohexylmethylmalonate produced in Step A4a This Step is carried out using the standard literature method for the hydrolysis and subsequent decarboxylation of diethyl alkylmalonates which is described in the article by E. C. Vliet, C. S. Marvel and C. M. Hsueh in Organic Syntheses, Collective Volume II, page 416. The product 3-(trans-4'-n-pentylcyclohexyl)propanoic acid (yield 71%) has mp=85°–87° C.

Step A6a

The production of 3-(trans-4'-pentylcyclohexyl) propanals from the corresponding propanoic acid produced in Step A5a This Step is carried out using the standard literature method for the reduction of carboxylic acids to aldehydes as described in the article by T. Fujisawa et al in Tetrahedron Letters, 24, page 1543 (1983). The product 3-(trans-4'-n-pentylcyclohexyl)propanal (yield 73% has mp=103°–105° C. at 0.3 mm Hg.

Step A7a

The production of diethyl n-propylmalonate from the corresponding n-propyl bromide This Step is carried out using the standard literature method for the alkylation of diethyl malonate using the appropriate alkyl bromide described in Textbook of Practical Organic Chemistry by A. I. Vogel, 4th edition, page 491, (1978).

Step A8a

The production of 2-n-propylpropan-1,3-diol from the corresponding diethyl n-propylmalonate This Step is carried out using the standard literature method for the reduction of a diester to a diol described in Textbook of Practical Organic Chemistry by A. I. Vogel, 4th edition, page 362, (1978).

Step A9a

The production of 2-(trans-4'-n-pentylcyclohexylethyl)-5-n-propyl-1,3-dioxan from the products of Steps A6a and A8a A mixture of the 2-n-propylpropan-1,3-diol (0.007 mole), the 3-trans-4'-pentylcyclohexyl)propanal (0.007 mole), toluene-4-sulphonic acid (30 mg) and dry benzene (34 cm³) is heated under reflux for 2½ hours, using a Dean and Stark apparatus to eliminate the water produced during the course of the reaction. The solvent is removed in vacuo and the residue taken up in ether (80 cm³). The solution is washed with aqueous 2% sodium hydrogen carbonate (3×40 cm³), water (2×40 cm³), dried ($Na_2SO_4$) and filtered. The solvent is then removed in vacuo. The crude product is recrystallised from methanol to yield the trans-isomer (the cis-isomer remaining in the mother liquors). The product 2-(trans-4'-n-pentylcyclohexylethyl)-5-n-propyl-1,3-dioxan has mp=44° C. and gives a monotropic nematic to isotropic transition at 42° C. determined by optical microscopy.

Examples of the transition temperatures of other compounds prepared analogously are as follows:

(i) The compound of formula

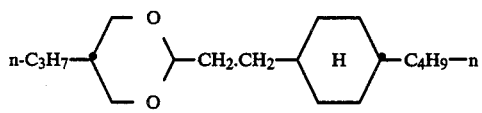

has mp=29° C., cp (clearing point or nematic to isotropic liquid transition temperature)=36° C. and a Smectic B-nematic transition at 25° C.

Examples of compounds which may be prepared by the method of Example 1 are listed in Table 1a as follows.

TABLE 1a

Compound of Formula I $R_1$—◇—$CH_2.CH_2$—⬡—$R_2$ (with O—O in dioxan ring)

| $R_1$ | $R_2$ | |
|---|---|---|
| $CH_3$ | n-$C_mH_{2m+1}$ | All values of m from 1 to 12 inclusive |
| $CH_3$ | (+)-2-methylbutyl | |
| $C_2H_5$ | n-$C_mH_{2m+1}$ | All values of m from 1 to 12 inclusive |

TABLE 1a-continued

Compound of Formula I

| $R_1$ | $R_2$ | |
|---|---|---|
| $C_2H_5$ | (+)-2-methylbutyl | |
| n-$C_3H_7$ | n-$C_mH_{2m+1}$ | All values of m from 1 to 12 inclusive |
| n-$C_3H_7$ | (+)-2-methylbutyl | |
| n-$C_4H_9$ | n-$C_mH_{2m+1}$ | All values of m from 1 to 12 inclusive |
| n-$C_4H_9$ | (+)-2-methylbutyl | |
| n-$C_5H_{11}$ | n-$C_mH_{2m+1}$ | All values of m from 1 to 12 inclusive |
| n-$C_5H_{11}$ | (+)-2-methylbutyl | |
| n-$C_6H_{13}$ | n-$C_mH_{2m+1}$ | All values of m from 1 to 12 inclusive |
| n-$C_6H_{13}$ | (+)-2-methylbutyl | |
| n-$C_7H_{15}$ | n-$C_mH_{2m+1}$ | All values of m from 1 to 12 inclusive |
| n-$C_7H_{15}$ | (+)-2-methylbutyl | |
| n-$C_8H_{17}$ | n-$C_mH_{2m+1}$ | All values of m from 1 to 12 inclusive |
| n-$C_8H_{17}$ | (+)-2-methylbutyl | |
| n-$C_9H_{19}$ | n-$C_mH_{2m+1}$ | All values of m from 1 to 12 inclusive |
| n-$C_9H_{19}$ | (+)-2-methylbutyl | |
| n-$C_{10}H_{21}$ | n-$C_mH_{2m+1}$ | All values of m from 1 to 12 inclusive |
| n-$C_{10}H_{21}$ | (+)-2-methylbutyl | |
| n-$C_{11}H_{23}$ | n-$C_mH_{2m+1}$ | All values of m from 1 to 12 inclusive |
| n-$C_{11}H_{23}$ | (+)-2-methylbutyl | |
| n-$C_{12}H_{25}$ | n-$C_mH_{2m+1}$ | All values of m from 1 to 12 inclusive |
| n-$C_{12}H_{25}$ | (+)-2-methylbutyl | |

EXAMPLE 2

Use of Route B shown in FIG. 3 to prepare the compound of Formula Ib (FIG. 1) having $R_1$=n—$C_5H_{11}$ and $R_2$=R=n—$C_3H_7$. Steps B 1a etc are examples of Steps B1 etc.

Step B1a

The production of trans-4-n-pentylcyclohexylmethyl bromide from the corresponding trans-4-n-pentylcyclohexyl methanol (prepared from 4-n-pentylcyclohexane-1-carboxylic acid by the method described above in Steps A1a and A2a of Example 1)

This Step B1a is carried out using the standard literature method for the conversion of alcohols into alkyl bromides as described in Textbook of Practical Organic Chemistry by A. I. Vogel, 4th edition, page 387, (1978). The product trans-4-n-pentylcyclohexylmethyl bromide has a bp=165° C. (at 25 mm Hg).

Step B2a

The production of 3-(trans-4'-pentylcyclohexyl) propionitriles from the appropriate trans-4-n-pentylcyclohexylmethyl bromide Ethyl cyanoacetate (10.308 mole) is added dropwise to a stirred solution of sodium ethoxide in ethanol (prepared by running dry ethanol (250 cm³) onto sodium metal (0.308 g atom)). The mixture is then heated to reflux and the trans-4-n-pentylcyclohexyl bromide is added dropwise. When the addition is complete the mixture is heated at reflux for 3 hours. The ethanol is then removed in vacuo and the residue is poured into water (150 cm$^3$). The mixture is shaken with ether (3×6 cm$^3$ and the combined ethereal phases are washed with water (2×60 cm$^3$), dried (MgSO$_4$) and filtered. The solvent is then removed in vacuo.

The crude ester is then added to cold aqueous 10% sodium hydroxide and the mixture is stirred at room temperature for 2 hours. At the end of this time the mixture is shaken with ether (60 cm$^3$) and then the aqueous phase is acidified with concentrated hydrochloric acid. The mixture is then shaken with ether (3×60 cm$^3$) and the combined ethereal phases are washed with water (3×60 cm$^3$), dried (MgSO$_4$), filtered, and the solvent is removed in vacuo.

The residue is then heated at 180° C. for 50 minutes until evolution of CO$_2$ ceases. The crude nitrile is then purified by distillation under reduced pressure. The product, 3-(trans-4'-n-pentylcyclohexyl) propionitrile has bp=86° C. at 0.5 mm Hg.

Step B3a

The production of 3-(trans-4'-n-pentylcyclohexyl)-1-ethoxypropyl-1-imine hydrochloride from the corresponding 3-(trans-4-n-pentylcyclohexyl) propionitrile This Step is carried out using the standard literature method for the production of ethoxy alkyl imine hydrochlorides from nitriles described in the article by A. Boller et al in Mol Cryst Liq Cryst, 42, page 215, (1977).

Step B4a

The production of 3-(trans-4'-n-pentylcyclohexyl) propyl amidine hydrochloride from the corresponding 3-(4'-trans-4'-n-pentylcyclohexyl)-1-ethoxypropyl-1-imine hydrochloride This Step is carried out using the standard literature method for the production of amidine hydrochlorides from ethoxy alkyl imine hydrochlorides described in the article by A. Boller et al in Mol Cryst Liq Cryst, 42, page 215 (1977).

Step B5a

The production of diethyl n-propylacetals from the corresponding propanal

This Step is carried out using a standard literature method for the production of diethyl acetals from aldehydes described in the article by A. Arentzen, Y. T. Yan Kui, and C. B. Reese, in Synthesis, page 509, (1975).

Step B6a

The production of 2-n-propyl-3-ethoxy propanals from the corresponding diethyl alkylacetal This Step is carried out using a standard literature method for the formulation of acetals as described in the article by Z. Arnold and F. Sorm, in Coll Chech Chem Comm 23, page 452, (1956).

Step B7a

The production of 2-(trans-4'-n-pentylcyclohexylethyl)-5-n-propyl pyrimidines from 3-(trans-4'-n-pentylcyclohexyl) propyl amidine hydrochloride and 2-n-propyl-3-ethoxy propenal This Step is carried out using the standard literature method for the production of pyrimidines from amidine hydrochlorides and 2-alkyl-3-ethoxy propenals as in the article by A. Boller et al in Mol Cryst Liq Cryst, 42, page 215, (1977).

EXAMPLE 3

Use of Route C shown in FIG. 4 to prepare the compound of Formula Id (FIG. 1) having R$_1$=n—C$_5$H$_{11}$ and R$_2$=OR=n—C$_3$H$_7$.

Step C1a

The production of diethyl n-propylmalonates from the corresponding ethyl n-propyloxyacetate This Step is carried out using the standard literature method for the production of diethyl alkoxymalonates as described in Chem Abstr, 64, 12.6.73 (1966).

Step C2a

The production of 2-(trans-4'-n-pentylcyclohexylethyl)-5-n-propyloxy-4,6-dihydroxypyrimidines from 3-(trans-4'-n-pentylcyclohexyl) propyl amidine hydrochloride produced in Step B4a and diethyl n-propyloxymalonate produced in Step C1a This Step is carried out using the standard literature method for the production of dihydroxypyrimidines from amidine hydrochlorides and diethyl alkoxymalonates as described in East German Patent Specification No. 95892.

Step C3a

The production of 2-(trans-4'-n-pentylcyclohexylethyl)-5-n-propyloxy-4,6-dichloropyrimidines from the corresponding 2-(trans-4'-n-pentylcyclohexylethyl)-5-n-propyloxy-4,6-dihydroxypyrimidine This Step is carried out using the standard literature method for the chlorination of hydroxypyrimidines as described in East German Patent Specification No. 95892.

Step C4a

The production of 2-(trans-4'-n-pentylcyclohexylethyl)-5-n-propyloxypyrimidine from the corresponding 2-(trans-4'-n-pentylcyclohexylethyl)-5-n-propyloxy-4,6-dichloropyrimidine This Step is carried out using the standard literature method for the catalytic dechlorination of dichloropyrimidines as described in East German Patent Specification No. 95892.

Examples of compounds which may be made by the methods of Example 1 and 2 are summarised in Table 1b as follows:

TABLE 1

Compounds of formula

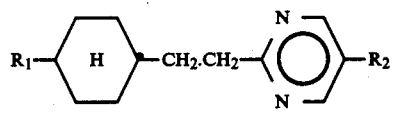

| R$_1$ | R$_2$ | |
|---|---|---|
| CH$_3$ | n-C$_m$H$_{2m+1}$ | For all values of m from 0 to 12 |
| CH$_3$ | n-C$_p$H$_{2p+1}$O | For all values of p from 1 to 12 |
| CH$_3$ | (+)-2-methylbutyl | |
| C$_2$H$_5$ | n-C$_m$H$_{2m+1}$ | For all values of m from 0 to 12 |
| C$_2$H$_5$ | n-C$_p$H$_{2p+1}$O | For all values of p from 1 to 12 |

TABLE 1-continued

Compounds of formula

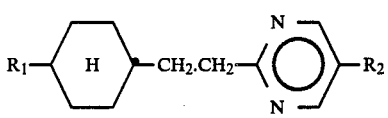

| $R_1$ | $R_2$ | |
|---|---|---|
| $C_2H_5$ | (+)-2-methylbutyl | |
| n-$C_3H_7$ | n-$C_mH_{2m+1}$ | For all values of m from 0 to 12 |
| n-$C_3H_7$ | n-$C_pH_{2p+1}$O | For all values of p from 1 to 12 |
| n-$C_3H_7$ | (+)-2-methylbutyl | |
| n-$C_4H_9$ | n-$C_mH_{2m+1}$ | For all values of m from 0 to 12 |
| n-$C_4H_9$ | n-$C_pH_{2p+1}$O | For all values of p from 1 to 12 |
| n-$C_4H_9$ | (+)-2-methylbutyl | |
| n-$C_5H_{11}$ | n-$C_mH_{2m+1}$ | For all values of m from 0 to 12 |
| n-$C_5H_{11}$ | n-$C_pH_{2p+1}$O | For all values of p from 1 to 12 |
| n-$C_5H_{11}$ | (+)-2-methylbutyl | |
| n-$C_6H_{13}$ | n-$C_mH_{2m+1}$ | For all values of m from 0 to 12 |
| n-$C_6H_{13}$ | n-$C_pH_{2p+1}$O | For all values of p from 1 to 12 |
| n-$C_6H_{13}$ | (+)-2-methylbutyl | |
| n-$C_7H_{15}$ | n-$C_mH_{2m+1}$ | For all values of m from 0 to 12 |
| n-$C_7H_{15}$ | n-$C_pH_{2p+1}$O | For all values of p from 1 to 12 |
| n-$C_7H_{15}$ | (+)-2-methylbutyl | |
| n-$C_8H_{17}$ | n-$C_mH_{2m+1}$ | For all values of m from 0 to 12 |
| n-$C_8H_{17}$ | n-$C_pH_{2p+1}$O | For all values of p from 1 to 12 |
| n-$C_8H_{17}$ | (+)-2-methylbutyl | |
| n-$C_9H_{19}$ | n-$C_mH_{2m+1}$ | For all values of m from 0 to 12 |
| n-$C_9H_{19}$ | n-$C_pH_{2p+1}$O | For all values of p from 1 to 12 |
| n-$C_9H_{19}$ | (+)-2-methylbutyl | |
| n-$C_{10}H_{21}$ | n-$C_mH_{2m+1}$ | For all values of m from 0 to 12 |
| n-$C_{10}H_{21}$ | n-$C_pH_{2p+1}$O | For all values of p from 1 to 12 |
| n-$C_{10}H_{21}$ | (+)-2-methylbutyl | |
| n-$C_{11}H_{23}$ | n-$C_mH_{2m+1}$ | For all values of m from 0 to 12 |
| n-$C_{11}H_{23}$ | n-$C_pH_{2p+1}$O | For all values of p from 1 to 12 |
| n-$C_{11}H_{23}$ | (+)-2-methylbutyl | |
| n-$C_{12}H_{25}$ | n-$C_mH_{2m+1}$ | For all values of m from 0 to 12 |
| n-$C_{12}H_{25}$ | n-$C_pH_{2p+1}$O | For all values of p from 1 to 12 |
| n-$C_{12}H_{25}$ | (+)-2-methylbutyl | |
| (+)-2-methylbutyl | n-$C_mH_{2m+1}$ | For all values of m from 0 to 12 |
| (+)-2-methylbutyl | n-$C_pH_{2p+1}$ | For all values of p from 1 to 12 |
| (+)-2-methylbutyl | (+)-2methylbutyl | |

Examples of the transition temperatures of compounds made by Route B are as follows:
The compound of formula

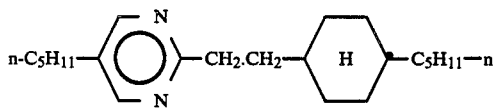

has mp=42.5° C. and cp=[−20° C.] (virtual transition).

Further properties of compounds of Formula I are described as follows.

The birefringence Δn of a compound of formula I has been measured and it is very low. The results over the nematic temperature range are shown in Table R1 as follows:

TABLE R1

Birefringence of the compound of formula:

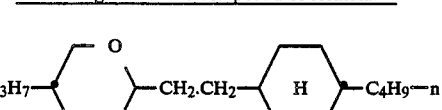

| Temperature (°C.) | Δn |
|---|---|
| 29.6 | 0.03318 |
| 31.8 | 0.03209 |
| 34.1 | 0.02887 |

TABLE R1-continued

Birefringence of the compound of formula:

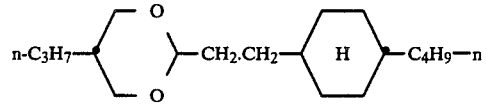

| Temperature (°C.) | Δn |
|---|---|
| 35.6 | 0.02504 |

The effect of adding the compound of formula

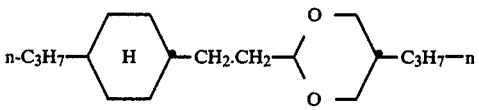

to the commercially available material ZLI 1289 (from E Merck Co) has been studied. The elastic constant ratio $k_{33}/k_{11}$ is reduced by the addition (30% by weight of the compound of formula

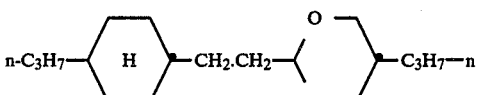

and 70% by weight of ZLI 1289. Gamma $\epsilon_\perp/\Delta\epsilon$ is also lower.

The extrapolated nematic viscosity of two formula I compounds has been measured in (i) the commercially available nematic material ZLI 1132 (from E Merck Co) and in the material I32/I35/I52: a mixture of equal weights of the compounds of formulae:

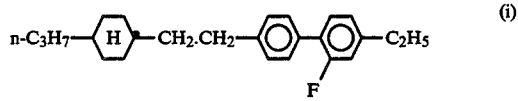

(i)

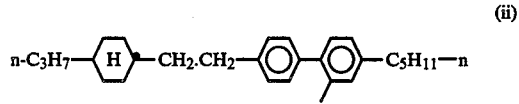

(ii)

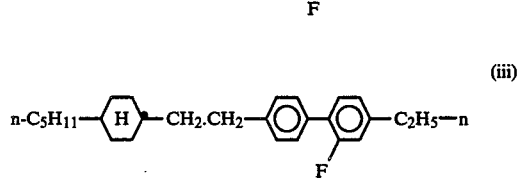

(iii)

The results are given in Table R2 as follows:

TABLE R2

Properties of mixtures containing the compounds of formula

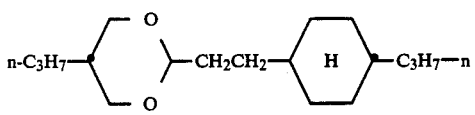

R₁—[dioxane]—CH₂.CH₂—[H]—R₂ (Viscosities in cps)

| R₁ | R₂ | Host material → Temperature | ZLI 1132 Viscosity | I 32/35/52 Viscosity |
|---|---|---|---|---|
| n-C$_3$H$_7$ | n-C$_3$H$_7$ | 20° C. | 23.5 | 23.4 |
|  |  | 0° C. | 65.5 | 62.2 |
| n-C$_5$H$_{11}$ | n-C$_3$H$_{11}$ | 20 C. | — | 31.2 |
|  |  | 0° C. | — | 112.6 |

Properties of the compound of formula:

n-C$_3$H$_7$—[dioxane]—CH$_2$CH$_2$—[H]—C$_3$H$_7$—n (30% by weight) mixed with the commercially available host material ZLI 1289 from Merck Co (70% by weight) relevant to multiplexing are given in Table R3 as follows where the parameters listed are those well known in the art (and are defined for example in UK Patent Specification No. 2097418A).

TABLE R3

Properties of mixture

| Property of mixture | Result |
|---|---|
| Clearing point (°C.) | 52 |
| V$_{90}$ (45°, 20° C.) (volts) | 1.01 |
| M$_{20}$ | 1.92 |
| M$^T_{20}$ | 1.41 |
| $\frac{1}{V}\frac{dV}{dT}$ 0→40 (%/°C.) | 0.96 |

Examples of materials and devices embodying the invention will now be described by way of example only with reference to the accompanying drawings wherein.

Figure 1:
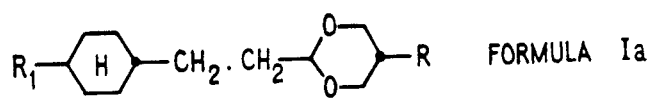
Figure 1:
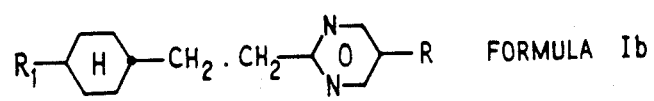
Figure 1:
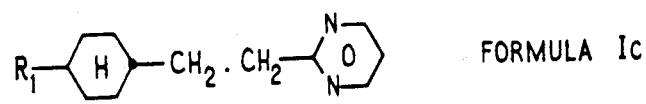
Figure 1:
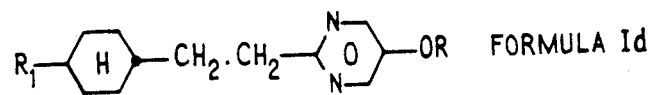
Figure 2:
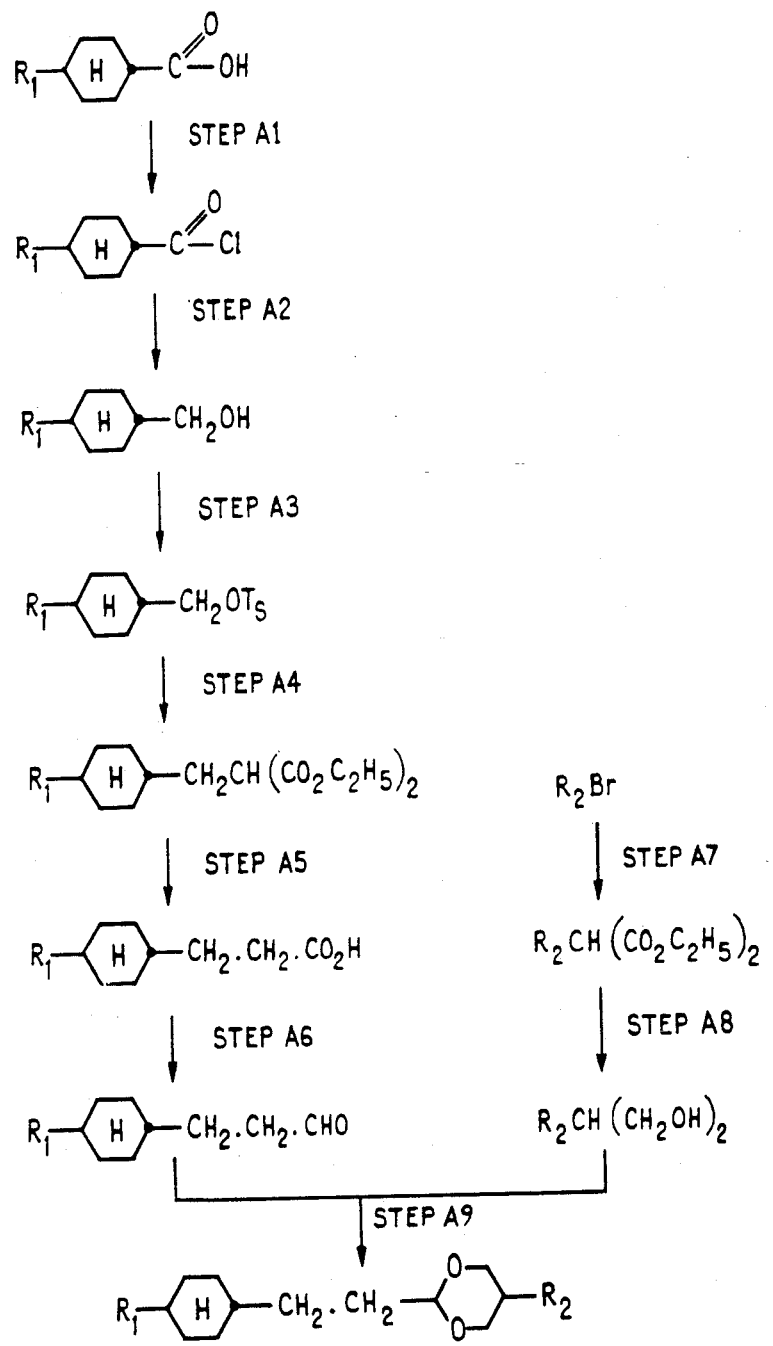

The display of FIGS. 9 to 12 comprises a cell 1, formed of two, front and back, glass slides 2, 3 respectively, spaced about 7 μm apart by a spacer 4 all held together by an epoxy resin glue. A liquid crystal material 12 fills the gap between the slides 2, 3 and the spacer 4. In front of the front glass slide 2 is a front polariser 5 arranged with its axis of polarisation axis horizontal. A reflector 7 is arranged behind the slide 3. A rear polariser 6 or analyser is arranged between the slide 3 and reflector 7.

Figure 3:
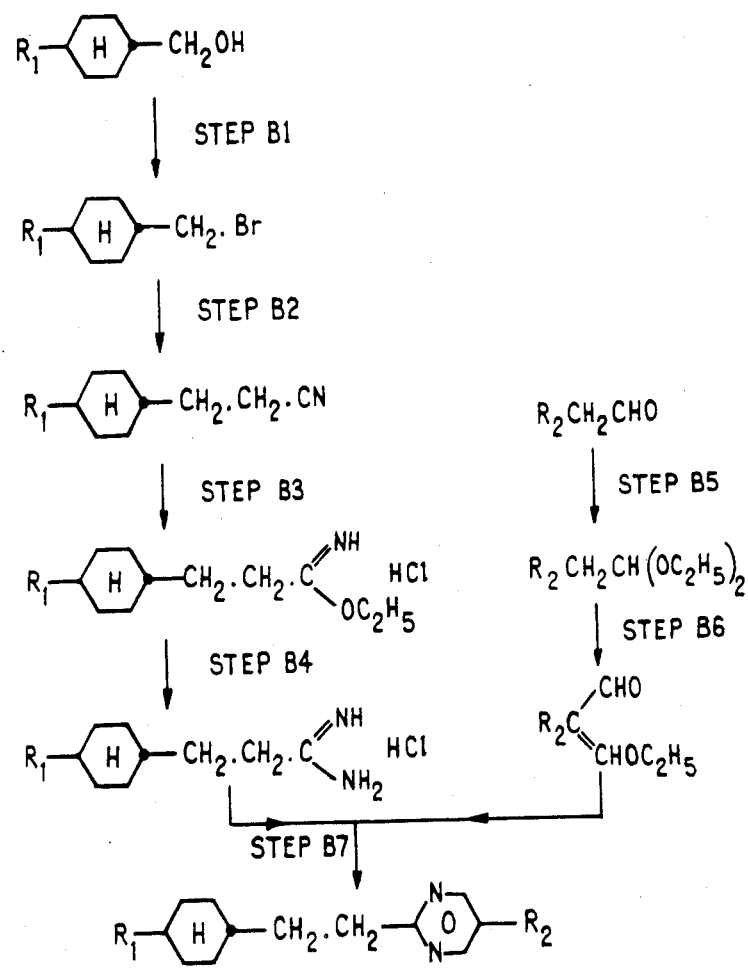
Figure 4:
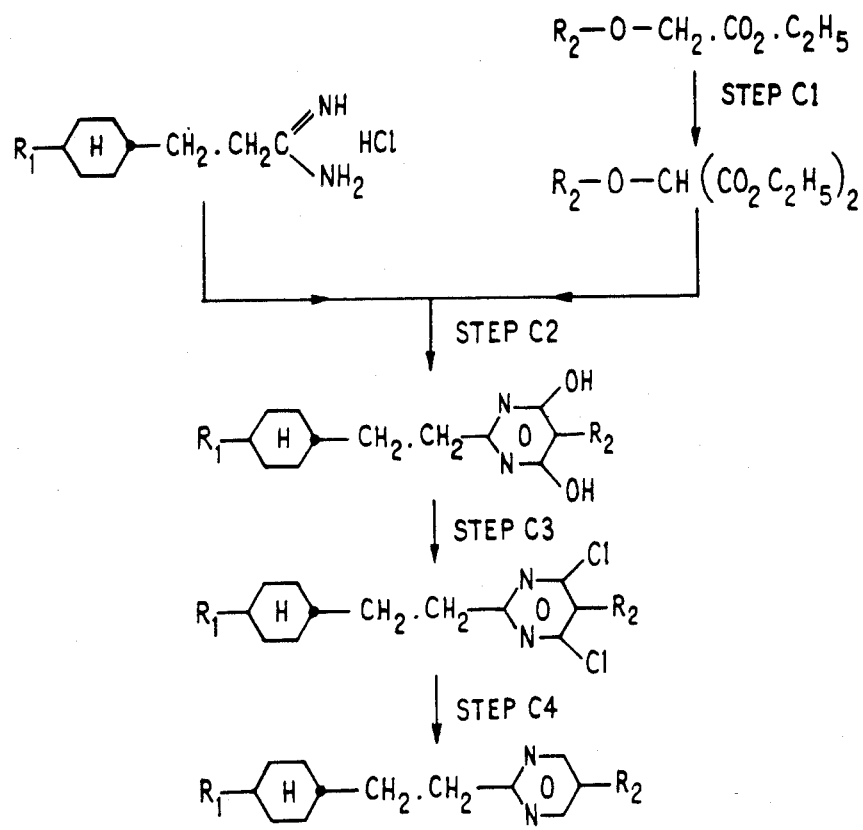
Figure 5:
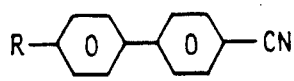
Figure 5:
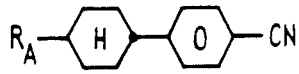
Figure 5:
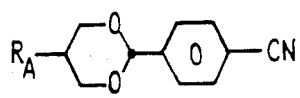
Figure 5:
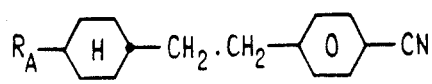
Figure 5:
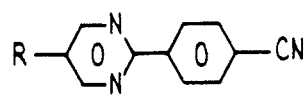
Figure 5:
Figure 5:
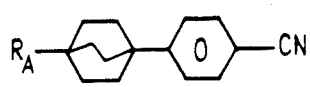
Figure 5:
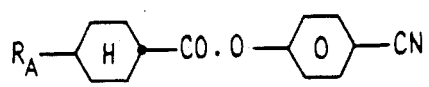
Figure 5:
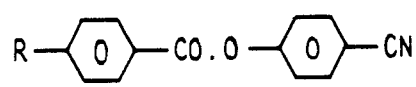
Figure 6:
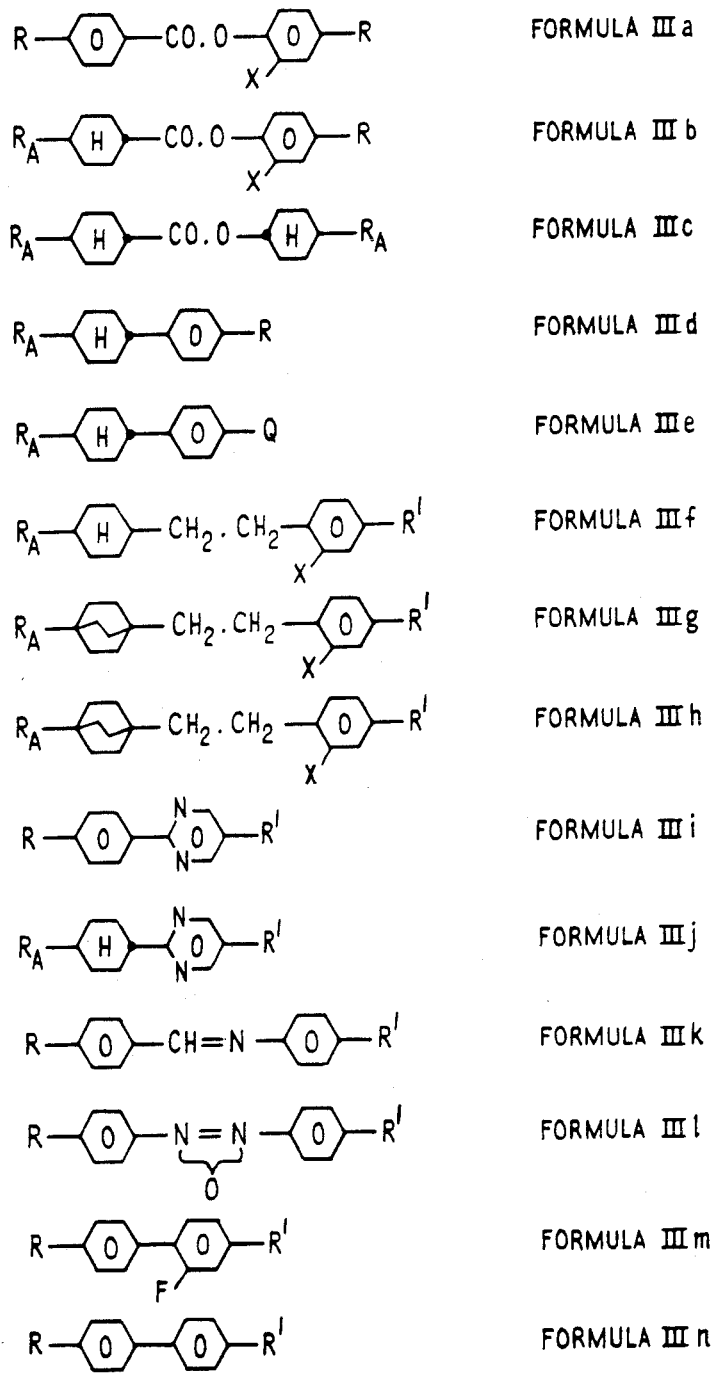
Figure 7:
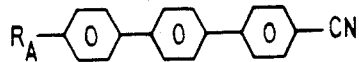
Figure 7:
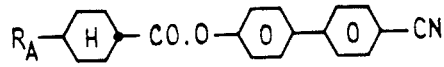
Figure 7:
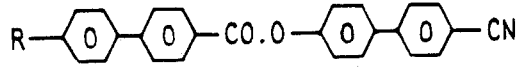
Figure 7:
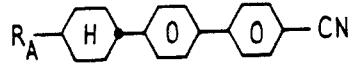
Figure 7:
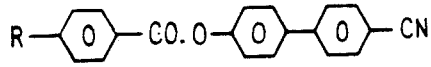
Figure 7:
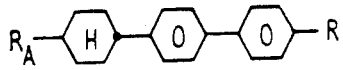
Figure 7:
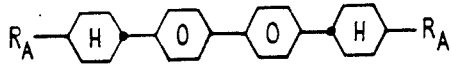
Figure 7:
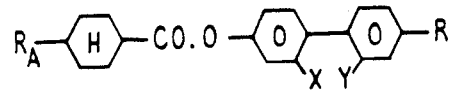
Figure 7:
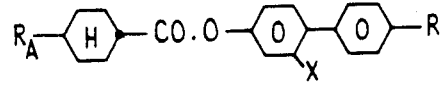
Figure 7:
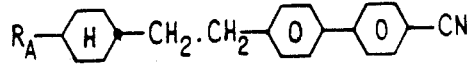
Figure 7:
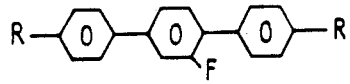
Figure 7:
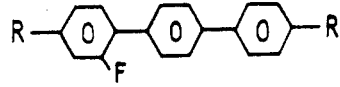
Figure 7:
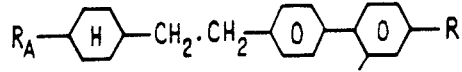
Figure 7:
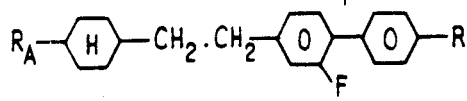
Figure 8:
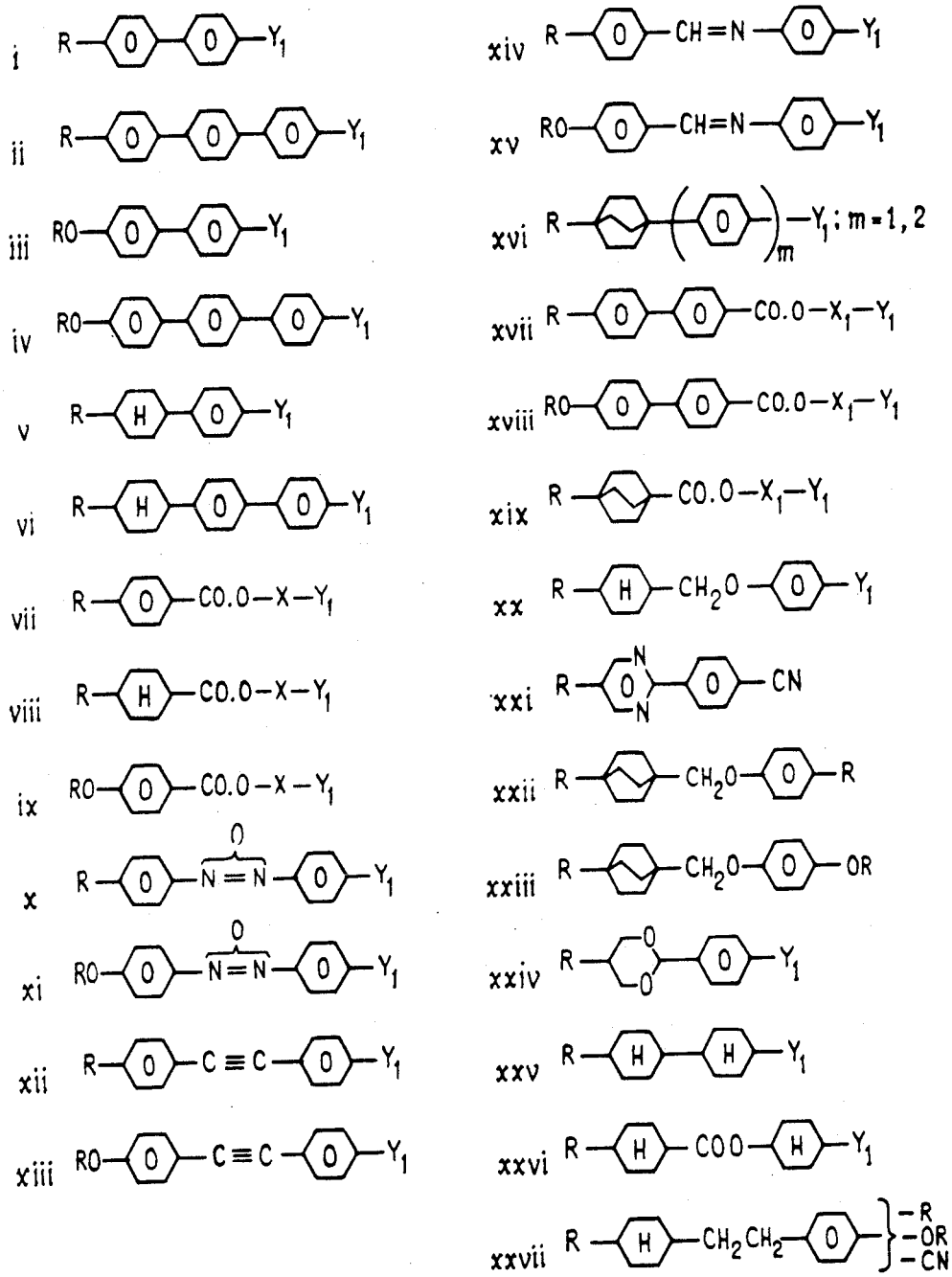
Figure 9:
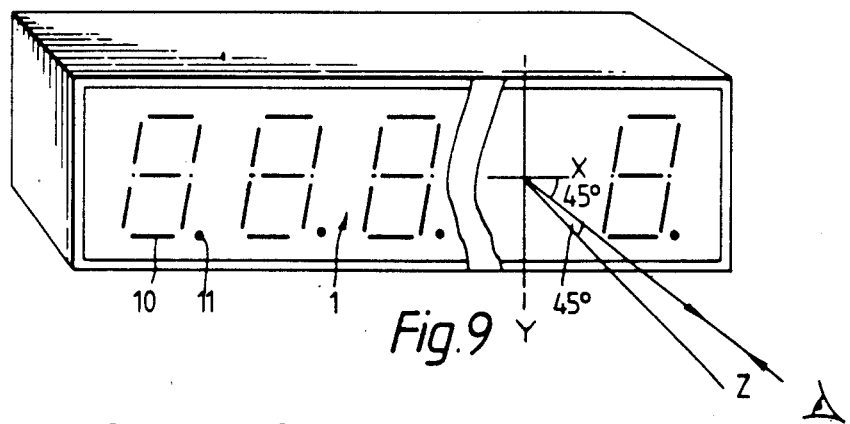
FIG. 9 is a sectional view of a twisted nematic digital display.
Figure 10:
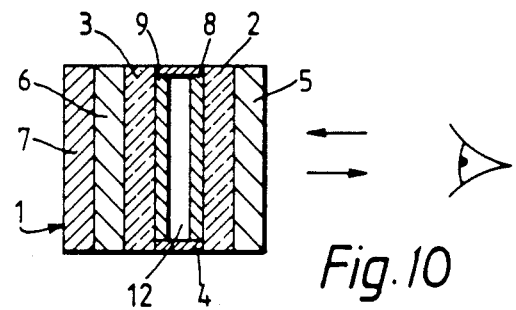
FIG. 10 is a sectional view of the display shown in FIG. 9.
Figure 11:
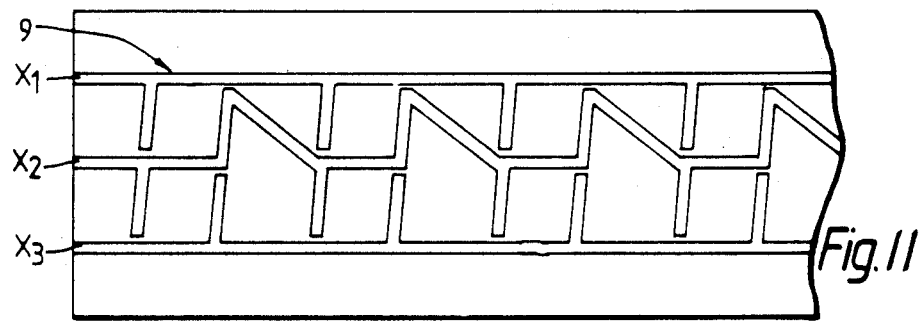
FIG. 11 shows a rear electrode configuration for FIG. 1.
Figure 12:
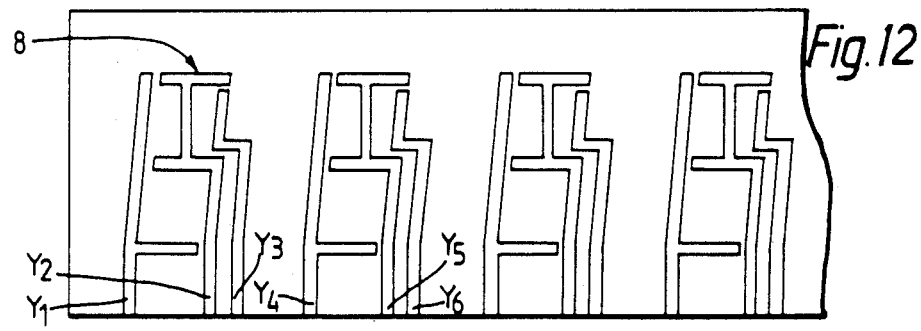
FIG. 12 shows a front electrode configuration for FIG. 1.

Electrodes 8, 9 of tin oxide typically 100 Å thick are deposited on the inner faces of the slides 2, 3 as a complete layer and etched to the shapes shown in FIGS. 3, 4. The display has seven bars per digit 10 plus a decimal point 11 between each digit. As shown in FIG. 3 the rear electrode structure is formed into three electrodes x$_1$, x$_2$, x$_3$. Similarly the front electrode structure is formed into three electrodes per digit and decimal point y$_1$, y$_2$, y$_3$... Examination of the six electrodes per digit shows that each of the eight elements can independently have a voltage applied thereto by application of suitable voltages to appropriate x, y electrodes.

Prior to assembly the slides 2, 3 bearing the electrodes are cleaned then dipped in a solution of 0.2% by weight of poly-vinyl alcohol (PVA) in water. When dry, the slides are rubbed in a single direction with a soft tissue then assembled with the rubbing directions orthogonal to one another and parallel to the optical axis of the respective adjacent polarisers, i.e. so that the polarisers are crossed. When the nematic liquid crystal material 12 is introduced between the slides 2, 3 the molecules at the slide surfaces lie along the respective rubbing directions with a progressive twist between the slides.

When zero voltage is applied to the cell 1 light passes through the front polariser 5, through the cell 1 (whilst having its plane of polarisation rotated 90°) through its rear polariser 6 to the reflector 7 where it is reflected back again to an observer (shown in FIG. 1 at an angle of 45° to the axis Z normal to axes X and Y in the plane of the slides 2, 3). When a voltage above a threshold value is applied between two electrodes 8, 9 the liquid crystal layer 12 loses its optical activity, the molecules being re-arranged to lie perpendicular to the slides 2,3, i.e. along the axis Z. Thus incident light at the position shown does not reach the reflector 7 and does not reflect back to the observer who sees a dark display of one or more bars of a digit 10.

Figure 13:
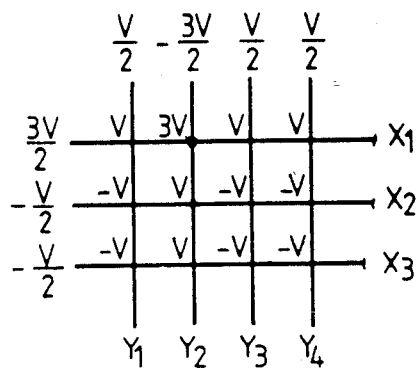
FIGS. 13, 14 and 15 show schematic views of the device of FIGS. 9 to 12 with typical addressing voltages.
Figure 14:
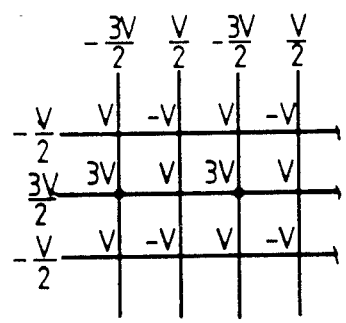
Figure 15:
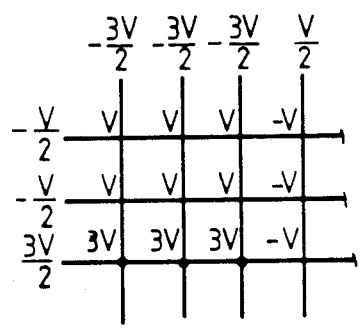

Voltages are applied as follows as shown in FIGS. 13, 14 and 15 for three successive time intervals in a linescan fashion. An electrical potential of 3V/2 is applied to, i.e. scanned down, each x electrode in turn whilst −V/2 is applied to the remaining x electrodes. Meanwhile −3V/2 or V/2 is applied to the y electrodes. A coincidence of 3V/2 and −3V/2 at an intersection results in a voltage 3 V across the liquid crystal layer 12. Elsewhere the voltage is V or −V. Thus by applying −3V/2 to appropriate y electrodes as 3V/2 is scanned down the x electrodes selected intersections are turned ON as indicated by solid circles. The electric voltage V is an ac signal of e.g. 100 Hz square wave, and the sign indicates the phase.

It will be apparent to those skilled in the art that the device shown in FIGS. 9 to 15 is a multiplexed display because the electrodes are shared between ON and OFF intersections or display elements.

Material embodying the invention which are suitable for use as the material 12 in the above device is Mixture 1 specified in Table 12 as follows.

TABLE 12

Mixture 1

| Compound | Weight Percentage |
|---|---|
| C₂H₅—⌬—⌬—CN | 15 |
| n-C₄H₉—⌬—⌬—CN | 15 |
| C₂H₅—⟨H⟩—⌬—CN | 15 |
| n-C₄H₉—⟨H⟩—⌬—CN | 15 |
| n-C₃H₇—⟨H⟩—CH₂.CH₂—⌬—⌬—C₃H₇—n (with F) | 20 |
| n-C₅H₁₁—⟨H⟩—CH₂.CH₂—⟨O⟩—C₃H₇—n (dioxane) | 20 |

Small amounts of an optically active material may be added to the nematic material to induce a preferred twist in the molecules in the liquid crystal layer. This and the use of appropriate slide surface treatment removes the problems of display patchiness as taught in UK Patent Ser. Nos. 1,472,247 and 1,478,592.

Suitable optically active materials are:

C15: about 0.1–0.5% by weight and CB15: about 0.01% to 0.05% by weight.

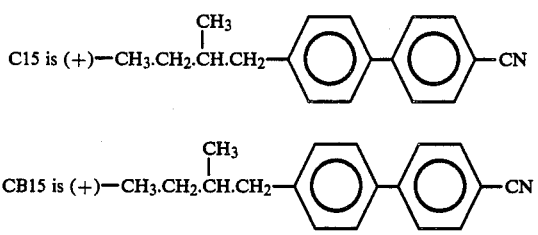

C15 is (+)—CH₃.CH₂.CH(CH₃).CH₂—⌬—⌬—CN

CB15 is (+)—CH₃.CH₂.CH(CH₃).CH₂—⌬—⌬—CN

Small amounts of pleochroic dye may be added to enhance the display contrast, e.g. 2% by weight of dye Mixture 2 specified in UK Patent Specification No. 2093475A. One polariser is removed in this case.

In another embodiment mixtures embodying the second aspect of the invention may be used in a Féedericksz effect cell. Such a cell may be constructed by sandwiching the liquid crystal material between glass slides having electrode films deposited on their inner surfaces as in the above device. However, in this case the polarisers are not necessary; the glass slide inner surfaces are treated with a coating of lecithin and the liquid crystal material is a negative material whose molecules are aligned in the OFF state perpendicular to the slide substrates (homeotropic texture) by the lecithin coating. Application of an appropriate electric field across the materil in the ON state re-arranges the molecules parallel to the slide surfaces (homogeneous texture). A pleochroic dye may be incorporated in the liquid crystal material to enhance the contrast between the ON and OFF states.

A Fréedericksz effect cell made in the above way may incorporate Mixture 3 below, the cell spacing being 10 μm.

TABLE 13

Mixture 3

| Compound | Weight Percentage |
|---|---|
| n-C₅H₁₁—⟨H⟩—CO.O—⌬(F)—C₃H₇—n | 30 |
| n-C₄H₉—⟨H⟩—CO.O—⌬(F)—C₅H₁₁—n | 30 |
| n-C₅H₁₁—⟨H⟩—CH₂.CH₂—⟨O⟩—C₃H₇—n (dioxane) | 20 |
| n-C₃H₇—⟨H⟩—CH₂.CH₂—⌬—⌬(F)—C₃H₇—n | 20 |

Compound J =

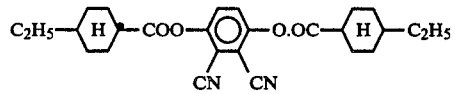

C₂H₅—⟨H⟩—COO—⌬(CN,CN)—O.OC—⟨H⟩—C₂H₅ may optionally be added to Mixture 3 (up to 3% by weight of Mixture 3) as a negative additive.

The preparation of Compound J is described in published UK Patent Application No. 2061256A. About 1% by weight of a the dye mixture specified above may be aded to Mixture 3 to give a dyed mixture. (Mixture 3A)

When a voltage is applied across the cell, the colour changes from a weakly absorbing state to a strongly absorbing state.

In an alternative embodiment of the invention a (cholesteric-to-nematic) phase change effect device incorporates a material as defined above.

A cell is prepared containing a long helical pitch cholesteric material sandwiched between electrode-bearing glass slides as in the twisted nematic cell described above. However the polarisers and surface preparations for homogeneous alignment, e.g. treatment of the glass slide surfaces with SiO, are not used in this case.

If the glass slides are untreated and the liquid crystal material has a positive dielectric anisotropy (Δε) the liquid crystal material is in a twisted focal conic molecular texture in the OFF state which scatters light. The effect of an electric field applied between a pair of electrodes on the respective inner surface of the glass slides is to convert the region of liquid crystal material between the electrodes into the ON state which is a homeotropic nematic texture which is less scattering than the OFF state. This is a 'negative contrast' type of phase change effect device.

If the inner glass slide surfaces are treated, e.g. with a coating of lecithin, to give alignment perpendicular to those surfaces, and the liquid crystal material has Δε negative the material in the OFF state is in a homeotropic texture which has little scattering effect on incident light. If an electric field is applied between a pair of electrodes on the respective inner surfaces of the glass slides the region of liquid crystal material between the electrodes is converted to a twisted homogenous texture which scatters light (the ON state). This is a 'positive contrast' type of phase change effect device.

The contrast between the two states in each case may be enhanced by the addition of a small amount of a suitable pleochroic dye (e.g. 1% by weight of the dye mixture specified above in the case where Δε is positive) to the liquid crystal material.

A suitable positive dielectric anisotropy material, Mixture 4, embodying the invention for use in a phase change effect (negative contrast type) device is:

TABLE 14

| Mixture 4 | |
|---|---|
| Compound | Weight Percentage |
| Mixture B { C6H13—⌬—⌬—CN 37.5% ; n-C4H9—⌬—⌬—CN 37.5% ; n-C3H7O—⌬—⌬—CN 25% } | 50 |
| n-C5H11—[H]—CH2.CH2—(dioxane)—C3H7-n | 23 |
| CB15 = Rc—⌬—⌬—CN  (Rc = (+)-2-methylbutyl) | 4 |
| n-C3H7—[H]—CH2.CH2—⌬—⌬(F)—C3H7-n | 23 |

A suitable negative dielectric anisotropy material embodying the invention for use in a phase change effect (positive contrast type) device, Mixture 5, is as follows:

TABLE 15

| Mixture 5 | |
|---|---|
| Material | Weight Percentage |
| Mixture 3 | 99 |

TABLE 15-continued

| Mixture 5 | |
|---|---|
| Material | Weight Percentage |
| 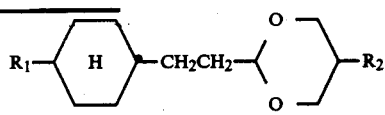 Rc—⌬—⌬—CO.O—⌬—Rc  (Rc = (+)-2-methylbutyl) | 1 |

We claim:

1. A heterocyclically substituted ethane having a formula:

R1—[H]—CH2CH2—(dioxane)—R2 wherein

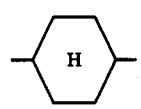

represents a trans - 1,4 disubstituted cyclohexyl ring;

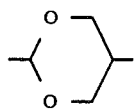

represents a trans - 2, 5 disubstituted 1, 3 - dioxan ring;

R$_1$ represents an alkyl group having from 1 to 15 carbon atoms and

R$_2$ represents an alkyl group having from 1 to 15 carbon atoms.

2. An ethane as claimed in claim 1 and wherein R$_1$ and R$_2$ each independently represent n - alkyl having from 1 to 10 carbon atoms.

3. A liquid crystal material which is a composition comprising a mixture of compounds at least one of which is an ethane as claimed in claim 1.

4. A liquid crystal device including two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein, characterised in that the liquid crystal material includes at least one ethane as claimed in claim 1.

* * * * *